(12) United States Patent
Gaudernack et al.

(10) Patent No.: US 6,861,057 B2
(45) Date of Patent: *Mar. 1, 2005

(54) IMMUNOGENIC β-AMYLOID PEPTIDE

(75) Inventors: Gustav Gaudernack, Sandvika (NO); Jon Amund Eriksen, Porsgrunn (NO); Mona Møller, Porsgrunn (NO)

(73) Assignee: GemVax AS, Oslo (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 284 days.

(21) Appl. No.: 09/674,913

(22) PCT Filed: Apr. 30, 1999

(86) PCT No.: PCT/NO99/00141

§ 371 (c)(1),
(2), (4) Date: May 25, 2001

(87) PCT Pub. No.: WO99/58564

PCT Pub. Date: Nov. 18, 1999

(65) Prior Publication Data

US 2003/0171266 A1 Sep. 11, 2003

(30) Foreign Application Priority Data

May 8, 1998 (NO) .......................................... 19982098

(51) Int. Cl.$^7$ ............................ C07K 7/00; A61K 39/00

(52) U.S. Cl. .................... 424/184.1; 530/300; 530/326; 424/185.1; 514/2

(58) Field of Search .............................. 514/2; 530/300, 530/326; 424/184.1, 185.1

(56) References Cited

U.S. PATENT DOCUMENTS

| | | | | |
|---|---|---|---|---|
| 5,780,587 A | * | 7/1998 | Potter | 530/326 |
| 5,851,996 A | * | 12/1998 | Kline | 514/12 |
| 5,958,684 A | * | 9/1999 | Van Leeuwen et al. | 435/6 |

FOREIGN PATENT DOCUMENTS

| | | | | |
|---|---|---|---|---|
| WO | WO 92/14756 | | 9/1992 | |
| WO | WO 95/32731 | | 12/1995 | |
| WO | WO 97/12992 | * | 4/1997 | ............ C12Q/1/68 |
| WO | WO 98/45322 | | 10/1998 | |
| WO | WO 99/58552 | | 11/1999 | |
| WO | WO 01/40804 A2 | * | 6/2001 | .......... G01N/33/68 |
| WO | WO 01/42306 | * | 6/2001 | ......... C07K/14/705 |

OTHER PUBLICATIONS

Skolnick and Fetrow (2000) From Genes to Protein Strucuture and Function: Novel Applications of Compuational Approaches in the Genomic Era. Trends in Biotech 18(1); 34–39.*

Jobling et al. (1991) Analysis of structure and function of the B subunit of cholera toxin by the use of site–directed mutagenesis. Mol. Microbiol. 5(7):1755–67.*

Monsonego et al. (2001) Immune Hyporesponsiveness to amyloid beta–peptide in amyloid precursor protein transgenic mice: Implicaitons for the pathogenesis and treatment of Alzheimer's disease. PNAS 98(18): 10273–10278.*

DeMattos et al. (2001) "Peripheral Anti Abeta Antibody Alters CNS and Plasma Abeta Clearance and Decreases Brain Abeta Bruden in a Mouse Model of Alzheimer's Disease" PNAS 10: 1–6.*

Esiri (2001) Is an Effective Immune Intervention for Alzheimer's Disease in Prospect? Trends in Pharm Science 22(1): 2–3.*

Younkin (2001) Amyloid beta Vaccination: Reduced Plaques and Improved Cognition. Nature Medicine 7(1):18–19.*

Games et al. (1995) Alzheimer–type Neuropathology in Transgenic Mice Overexpressing V717F beta–amyloid precursor protein. Nature 373(6514): 523–527.*

Schenk et al. (1999) Immunization with amyloid–beta attenuates Alzheimer–disease–like pathology in the PDAPP Mouse. Nature 400:173–177.*

Small et al. (2001) Alzheimer's Disease and Abeta Toxicity: from top to bottom. Nat Rev Neurosci. 2(8): 595–8.*

Chapman (2000) Model Behavior. Nature 408: 915–916.*

Grubeck–Lobenstein et al. (2000) Immunization of beta–amyloid: could T–cell activation have a harmful effect? TINS 23: 114.*

Friedland et al. (1997) Neuroimaging of Vessel Amyloid in Alzheimer's Disease in Cerebrovascular Pathology in Alzheimer's Disease, eds. de la Torre and Hachinski, New York Academy of Science, NY, NY.*

Frenkel et al. (1998) N–terminal EFRH Sequence of Alzheimer's beta–amyloid peptide represents the epitope of its anti–aggregating antibodies. Journal of Neuroimmunology 88: 85–90.*

Frenkel et al. (2000) Immunization against Alzheimer's beta–amyloid plaques via EFRH phage adminstration. PNAS 97(21) 11455–11459.*

Frenkel et al. (1999) High Affinity Binding of Monoclonal Antibodies to the sequential epitope EFRH of beta–amyloid peptide is essential for modulation of fibrillar aggregation. Journal of Neuroimmunology 95: 136–142.*

(List continued on next page.)

Primary Examiner—Elizabeth Kemmerer
Assistant Examiner—Christopher James Nichols
(74) Attorney, Agent, or Firm—Fitzpatrick, Cella, Harper & Scinto

(57) ABSTRACT

Frameshift Mutants β-Amyloid precursor peptides and mutant ubiquitin-B associated with Alzheimer's disease and Down syndrome eliciting T cellular immunity for use in compositions for the treatment and/or prophylaxis of Alzheimer's disease and/or Down syndrome.

2 Claims, No Drawings

OTHER PUBLICATIONS

ELAN "Elan and AHP Provide an Update on the Phase 2A Clinical Trial of AN–1792." Press Release (Jan. 28, 2002) and ELAN "Elan and Wyeth Provide Update on Status of Alzheimer's Collaboration" Press Release (Mar. 1, 2002).*

Tanaka et al. (1998) NC–1900, an active Fragment analog of arginine vasopressin, improves learning and memory deficits induced by beta–amyloid protein in rats. European Journal of Pharmacology 352: 135–142.*

Tennet et al. (1995) Serum amyloid P component precents proteolysis of the amyloid fibrils of Alzheimer disease and systemic amyloidosis. PNAS 92: 4299–4303.*

Chen et al. (1998) Neurodegenerative Alzheimer–like pathology in PDAPP 717V—F transgenic mice. Progress in Brain Research 117: 327–334.* van Leeuwen et al., ( Jan., 1998), Science 279:242–247, "Frameshift Mutants of β Amyloid Precursor Protein and Ubiquitin–B in Alzheimer's and Down Patients".

Vogel, (1998), Science 229:174, "Possible New Cause of Alzheimer's Disease Found".

Gaudernack, (1996), Immunotechnology 2:3–9, "T cell responses against mutant ras: a basis for novel cancer vaccines".

Gjertsen et al. (1996), Int. Jounal of Cancer 65:450–453, "Ex Vivo ras Peptide Vaccination in Patients with Advanced Pancreatic Cancer: Results of a Phase I/II Study".

Gjertsen et al. (1997), Int. J. Cancer 72:784–790, "Cytotoxic $CD4^+$ and $CD8^+$ T–Lymphocyt s, Generated by Mutant p21–ras (12Val) Peptide Vaccination of a Patient, Recognize . . . Tumour Cells Carrying This Mutation".

Gertsen et al. (1998) Vox Sanguinis 74(suppl. 2): 489–495, "Mutated Ras Peptides as Vaccines in Immunotherapy of Cancer".

Terry et al., Alzheimer Disease, 1994, pp. 179–196, "Structural Basis of the Cognitiv Alterations in Alzheimer Disease".

Barinaga, Science, vol. 257, 1992, pp. 880–881, "Getting Some Backbone": How MHC Binds Peptides.

Deres et al., Nature, vol. 342, 1989, pp. 561–564, "In vivo priming of virus–specific cytotoxic T lymphocytes with synthetic lipopeptide vaccine".

Tighe et al., Immun. Today, vol. 19(2), 1998, pp. 89–97, "Gene vaccination: plasmid DNA is more than just a blueprint".

* cited by examiner

IMMUNOGENIC β-AMYLOID PEPTIDE

This application is a 371 of PCT/NO99/00141 filed 30 Apr. 1999 which claims priority to NORWAY 19982098 filed on 8 May 1998.

The present invention relates to peptides for treatment and/or prophylaxis of Alzheimer's disease and Down syndrome.

Alzheimer's disease and treatment of Down syndrome are both associated with frameshift mutations occurring at the transcriptional level or by posttranscriptional editing of RNA during the encoding of β-Amyloid precursor protein (βAPP) and ubiquitin-B (Ubi-B). Such frameshift mutations give rise to mutant βAPP and Ubi-B protein products which are characterised by aberrant protein sequences at the carboxyl terminus. Peptides covering, either completely or parts of, the aberrant parts of mutant βAPP or Ubi-B protein products elicit T cellular immunity and can therefore be useful in compositions for the treatment of Alzheimer's disease and Down syndrome. Further the peptides of this invention can be used as a prophylaxtic anti-Alzheimer's disease vaccine.

The invention also relates to DNA sequences encoding peptides corresponding to aberrant βAPP and Ubi-B protein sequences found in Alzheimer's disease and Down syndrome patients, and to vectors comprising at least one insertion site containing a DNA sequence encoding at least one such peptide.

Further the invention relates to methods for the treatment and/or prophylaxis of Alzheimer's disease by administration of at least one mutant βAPP and/or Ubi-B peptide or a recombinant virus vector comprising at least one insertion site containing a DNA sequence encoding at least one mutant βAPP and/or one mutant Ubi-B peptide.

The present invention represents a development of a treatment and/or prophylaxis for Alzheimer's disease based on the use of peptides to generate activation of the T cellular arm of the body's own immune system against cells producing mutant βAPP and Ubi-B protein products associated with Alzheimer's disease.

The development and use of the methods for treatment of Alzheimer's disease may also be directly applicable for treatment of patients with Down syndrome.

TECHNICAL BACKGROUND

Peptides corresponding to aberrant protein sequences resulting from frameshift mutations in genes in cancer cells elicit specific T cellular immunity and can be used as anti-cancer vaccines (ref. Norwegian patent applications filed at the same date as the present application by Norsk Hydro ASA). In the same manner peptides corresponding to aberrant protein sequences resulting from frameshift mutations associated with other diseases can be used to develop treatments of that diseases based on generation of specific T cellullar immunity.

Frameshift mutations result in completely new amino acid sequences in the C-terminal part of the proteins, prematurely terminating where a novel stop codon appears. This results in two important consequences:

1) The truncated protein resulting from the frameshift is generally nonfunctional, in most cases resulting in "knocking out" of an important cellular function. Aberrant proteins may also gain new functions such as the capacity to aggragate and form plaques. In both cases the frameshift results in disease.

2) The aberant new C-terminal amino acid sequence resulting from the frameshift is foreign to the body. It does not exist prior to the mutation, and it only exists in cells having the mutation.

Since the mutant part of the proteins proteins are completely novel and therefore foreign to the immune system of the carrier, they may be recognized by T-cells in the repertoire of the carrier. So far, nobody has focused on this aspect of frameshift mutations, and no reports exist on the characterization of frameshift peptides from coding regions of proteins as antigens. This concept is therefore novel and forms the basis for developing vaccines based on these sequences. It follows that such vaccines may also be used prophyllactively in persons who inherit defective genes or in other ways are disposed for frameshift mutations. Such vaccines will therefore fill an empty space in the therapeutic armament against inherited forms of disease.

It has been shown that single amino acid substitutions in intracellular "self"-proteins may give rise to tumour rejection antigens, consisting of peptides differing in their amino acid sequence from the normal peptide. The T cells which recognise these peptides in the context of the major histocompatibility (MHC) molecules on the surface of the tumour cells, are capable of killing the tumour cells and thus rejecting the tumor from the host.

In contrast to antibodies produced by the B cells, which typically recognise a free antigen in its native conformation and further potentially recognise almost any site exposed on the antigen surface, T cells recognise an antigen only if the antigen is bound and presented by a MHC molecule. Usually this binding will take place only after appropriate antigen processing, which comprises a proteolytic fragmentation of the protein, so that the resulting peptide fragment fits into the groove of the MHC molecule. Thereby T cells are enabled to also recognise peptides derived from intracellular proteins. T cells can thus recognise aberrant peptides derived from anywhere in the cells, in the context of MHC molecules on the surface of the cells, and can subsequently be activated to eliminate the cells harbouring the aberrant proteins.

M.Barinaga, Science, 257, 880–881, 1992 offers a short review of how MHC binds peptides. A more comprehensive explanation of the Technical Background for this Invention may be found in D. Male et al, Advanced Immunology, 1987, J. B. lippincott Company, Philadelphia. Both references are hereby included in their entirety.

The MHC molecules in humans are normally referred to as HLA (human leukocyte antigen) molecules. They are encoded by the HLA region on the human chromosome No 6.

The HLA molecules appear as two distinct classes depending on which region of the chromosome they are encoded by and which T cell subpopulations they interact with and thereby activate primarily. The class I molecules are encoded by the HLA A, B and C subloci and they primarily activate CD8+ cytotoxic T cells. The HLA class II molecules are encoded by the DR, DP and DQ subloci and primarily activate CD4+ T cells, both helper cells and cytotoxic cells.

Normally every individual has six HLA Class I molecules, usually two from each of the three groups A,B and C. Correspondingly, all individuals have their own selection of HLA Class II molecules, again two from each of the three groups DP, DQ and DR. Each of the groups A, B, C and DP, DQ and DR are again divided into several subgroups. In some cases the number of different HLA Class I or II molecules is reduced due to the overlap of two HLA subgroups.

All the gene products are highly polymorphic. Different individuals thus express distinct HLA molecules that differ from those of other individuals. This is the basis for the difficulties in finding HLA matched organ donors in transplantations. The significance of the genetic variation of the HLA molecules in immunobiology is reflected by their role as immune-response genes. Through their peptide binding capacity, the presence or absence of certain HLA molecules governs the capacity of an individual to respond to peptide epitopes. As a consequence, HLA molecules determine resistance or susceptibility to disease.

T cells may control the development and growth of cells producing abberant proteins by a variety of mechanisms. Cytotoxic T cells, both HLA class I restricted CD8+ and HLA Class II restricted CD4+, may directly kill cells carrying the appropriate antigens. CD4+ helper T cells are needed for cytotoxic CD8+ T cell responses as well as for antibody responses, and for inducing macrophage and LAK cell killing.

A requirement for both HLA class I and II binding is that the peptides must contain a binding motif, which usually is different for different HLA groups and subgroups. A binding motif is characterised by the requirement for amino acids of a certain type, for instance the ones carrying large and hydrophobic or positively charged side groups, in definite positions of the peptide so that a narrow fit with the pockets of the HLA binding groove is achieved. The result of this, taken together with the peptide length restriction of 8–10 amino acids within the binding groove, is that it is quite unlikely that a peptide binding to one type of HLA class I molecules will also bind to another type. Thus, for example, it may very well be that the peptide binding motif for the HLA-A1 and HLA-A2 subgroups, which both belong to the class I gender, are as different as the motifs for the HLA-A1 and HLA-B1 molecules.

For the same reasons it is not likely that exactly the same sequence of amino acids will be located in the binding groove of the different class II molecules. In the case of HLA class II molecules the binding sequences of peptides may be longer, and it has been found that they usually contain from 10 to 16 amino acids, some of which, at one or both terminals, are not a part of the binding motif for the HLA groove.

However, an overlap of the different peptide binding motifs of several HLA class I and class II molecules may occur. Peptides that have an overlap in the binding sequences for at least two different HLA molecules are said to contain "nested T cell epitopes". The various epitopes contained in a "nested epitope peptide" may be formed by processing of the peptide by antigen presenting cells and thereafter be presented to T cells bound to different HLA molecules. The individual variety of HLA molecules in humans makes peptides containing nested epitopes more useful as general vaccines than peptides that are only capable of binding to one type of HLA molecule.

Effective vaccination of an individual can only be achieved if at least one type of HLA class I and/or II molecule in the patient can bind a vaccine peptide either in it's full length or as processed and trimmed by the patient's own antigen presenting cells.

The usefulness of a peptide as a general vaccine for the majority of the population increases with the number of different HLA molecules it can bind to, either in its full length or after processing by antigen presenting cells.

In order to use peptides derived from an abberant protein resulting from mutational events in cells as vaccines ortherapeutic agents to generate CD4+ and/or CD8+ T cells, it is necessary to investigate the mutant protein in question and identify peptides that are capable, eventually after processing to shorter peptides by the antigene presenting cells, to stimulate T cells.

DEFINITION OF PROBLEM SOLVED BY THE INVENTION

At present no drug or other treatment is able to eliminate the cells producing the aberrant proteins responsible for the degenerative process in the brain of patients afflicted with Alzheimers disease. There is a continuing need for treatment and prophylaxis of Alzheimer's disease. The present invention will contribute to supply new peptides that can have use as treatment and prophylaxis of Alzheimer's disease. Our approach is aimed at directly eliminating the cells responsible for the degenerative process.

The peptides may also be applicable for treatment of patients with Down syndrome.

DEFINITION OF THE INVENTION

A main object of the invention is to obtain peptides corresponding to peptide fragments of aberrant βAPP and Ubi-B proteins found in Alzheimer's disease and/or Down syndrome patients which can be used to stimulate T cells.

Another main object of the invention is to develop a treatment for Alzheimer's disease based on the T cell immunity which may be induced in patients by stimulating their T cells either in vivo or ex vivo with the peptides according to the invention.

A third main object of the invention is to develop a vaccine to prevent the establishment of Alzheimer's disease based solely or partly on peptides corresponding to peptides of the present invention which can be used to generate and activate T cells which produce cytotoxic T cell immunity against cells producing the mutant βAPP and mutant Ubi-B proteins.

A fourth main object of the invention is to design a treatment or prophylaxis for Alzheimer's disease specifically adapted to a human individual in need of such treatment or prophylaxis, which comprises administering at least one peptide according to this invention.

A fifth object of the invention is to obtain a treatment for patients with Down syndrome using the same methods as for the treatment of Alzheimer's disease.

These and other objects of the invention are achieved by the attached claims.

Frameshift mutations can occur at the gene level, transcriptional level or by posttranscriptional editing of RNA and result in premature stop codons and therefore a deletion of sometimes large parts of the proteins. Aberrant proteins arising from frameshift mutations have generally not been considered to be immunogenic and have therefore not been considered as targets for immunotherapy. Thus it has now surprisingly been found that a group of new peptides corresponding to aberrant proteins resulting from frameshift mutations associated with Alzheimer's disease and Down syndrome are useful for eliciting T cell responses against cells producing such aberrant proteins.

Genes containing a mono nucleoside base repeat sequence, for example of deoxyadenosine bases, or a di-nucleoside base repeat sequence, for example of deoxycytosine-deoxythymidine units, are susceptible to frameshift mutations. The frameshift mutations occur, respectively, either by insertion of one or two of the mononucleoside base residue or of one or two of the di-nucleoside base unit in the repeat sequence, or by deletion of one or two of the mono-nucleoside base residue or of one or two of the di-nucleoside base unit from the repeat sequence. A frameshift mutation will from the point of mutation encode a protein with a new and totally different amino acid sequence as compared to the normal protein. This mutant protein with the new amino acid sequence at the carboxy end will be specific for all cells in which such frameshift mutations have occurred.

In the remainder of this specification and claims the denomination frameshift mutant peptides will comprise such proteins and peptide fragments thereof.

These peptides are at least 8 amino acids long and correspond to frameshift mutant βAPP and/or Ubi-B protein sequences associated with Alzheimer's disease and/or Down syndrome.

A peptide according to this invention is characterised in that it a) is at least 8 amino acids long and is a fragment of a mutant βAPP and/or Ubi-B protein arising from a frameshift mutation associated with Alzheimer's disease or Down syndrome; and b) consists of at least one amino acid of the mutant part of the mutant βAPP and/or Ubi-B protein; and c) comprises 0–10 amino acids corresponding to the carboxyl terminus of the normal part of the protein sequence preceding the amino terminus of the mutant sequence and may further extend to the carboxyl terminus of the mutant part of the protein as determined by a new stop codon generated by the relevant frameshift mutation; and d) induces, either in its full length or after processing by antigen presenting cells, T cell responses.

The peptides of this invention contain preferably 8–25, 9–20, 9–16, 8–12 or 20–25 amino acids. They may for instance contain 9, 12, 13, 16 or 21 amino acids.

It is most preferred that the peptides of the present invention are at least 9 amino acids long, for instance 9–18 amino acids long, but due to the processing possibility of the antigen presenting cells also longer peptides are very suitable for the present invention. Thus the whole mutant amino acid sequence may be used as a frameshift mutant peptide according to the present invention, if it comprises 8 amino acids or more. The invention further relates to a method for vaccination of a person disposed for Alzheimer's disease, consisting of administering at least one peptide of the invention one or more times in an amount sufficient for induction of T-cell immunity to the mutant βAPP and/or Ubi-B proteins.

The invention also relates to a method for treatment of a patient with Alzheimer's disease, consisting of administering at least one peptide of the invention one or more times in an amount sufficient for induction of T-cell immunity to the mutant βAPP and/or Ubi-B proteins.

The invention also relates to a method for treatment of a patient with Down syndrome, consisting of administering at least one peptide of the invention one or more times in an amount sufficient for induction of T-cell immunity to the mutant βAPP and/or Ubi-B proteins.

DETAILED DESCRIPTION OF THE INVENTION

In the present description and claims, the amino acids are represented by their one letter abbreviation as known in the art.

The peptides of the present invention are exemplified by the βAPP and Ubi-B frameshift mutations associated with Alzheimer's disease and Down syndrome:

In Alzheimer's and Down syndrome patients, intracellular and extracellular deposites of proteins in tangles, neurophil threads and neuritic plaques are correlated with neuronal dysfunction leading to dementia (R. D. Terry et al in *Alzheimer Disease*, R. D. Terry, R. Katzman, K. L. Bick, Eds. (Raven, New York, 1994) pp. 179–196). These protein deposits have been shown to contain forms of β amyloid precursor protein (βAPP) and ubiquitin-B (Ubi-B) that are aberrant in the carboxyl terminus, and it has further been shown that these aberrant protein sequences are results of frameshift mutations which probably occur at the transcriptional level or by posttranscriptional editing of RNA (F. W. van Leeuwen et al, Science, vol 279, pp. 242–247).

In the case of βAPP two frameshift mutations have been observed, one by deletion of the di-nucleoside deoxyguanosine-deoxyadenosine (GA) unit from the (ACC) GAGAGAGA(ATG) SEQ ID NO: 11 sequence in exon 9, and one by deletion of a GA unit from the (CAT) GAGAGA(ATG) SEQ ID NO: 12 sequence in exon 10. The mutant βAPP peptides resulting from these frameshift mutations are shown in table 1. The peptides with seq id nos 1 and 4 are the mutant part of the βAPP protein sequence and the peptides with seq id nos 2, 3 and 5 represent mutant peptides extended into the normal βAPP sequence at the amino terminus.

TABLE 1

|  |  |
| --- | --- |
|  | (SEQ ID NO: 13) |
| normal βAPP; | RLEAKHRERMSQVMREWEEAERQAKNLPK |
| seq id no 1; | NVPGHERMGRGRTSSKELA |
| seq id no 2; | RLEAKHRENVPGHERMGRGRTSSKELA |
| seq id no 3; | RLEAKHRENVPGHERMG |
| seq id no 4; | MGRGRTSSKELA |
| seq id no 5; | ERMSQVMRGRGRTS |

Also in the case of Ubi-B two frameshift mutations have been observed, one by deletion of the di-nucleoside deoxyguanosine-deoxythymidine (GT) unit from the (TCT) GAGAGGT(GGT) SEQ ID NO: 14 sequence in exon, and one by deletion of a di-nucleoside deoxycytosine-deoxythymidine (CT) unit from the (TCA)CTCT(GGA) SEQ ID NO: 15 sequence in exon 2. The mutant Ubi-B peptides resulting from these frameshift mutations are shown in table 2. The peptides with seq id nos 6 and 9 are the mutant part of the Ubi-B protein sequence and the peptides with seq id nos 7, 8 and 10 represent mutant peptides extended into the normal Ubi-B sequence at the amino terminus.

TABLE 2

|  |  |
| --- | --- |
|  | (SEQ ID NO: 16) |
| normal Ubi-B; | HLVLRLRGGMQIFVKTLTGKTITLEVEPSD |
| seq id no 6; | YADLREDPDRQDHHPGSGAQ |
| seq id no 7; | HLVLRLRGYADLREDPDRQDHHPGSGAQ |
| seq id no 8; | HLVLRLRGYADLREDPD |
| seq id no 9; | GGGAQ |
| seq id no 10; | TLTGKTITGGGAQ |

The mutant βAPP and Ubi-B proteins are only encoded for by cells in which corresponding frameshift mutations have occurred and are therefore targets for specific immunotherapy of Alzheimer's disease and Down syndrome.

According to the present invention, peptides corresponding to mutant βAPP and mutant Ubi-B proteins can be used to elicit T cellular immunity and specific killing of cells producing mutant βAPP and mutant Ubi-B proteins, which in Alzheimer's disease and Down syndrome patients are correlated with neuronal dysfunction leading to dementia.

Other peptides of the invention can be fragments of the peptides listed in the Tables 1 and 2 above. Such fragments are most preferred from 9–16 amino acids long and include at least one amino acid from the mutant part of the protein.

As used in this description and claims the term fragment is intended to specify a shorter part of a longer peptide or of a protein.

Synthesis

The peptides are synthesised by using continuous flow solid phase peptide synthesis. N-a-Fmoc-amino acids with appropriate side chain protection are used. The Fmoc-amino acids are activated for coupling as pentafluorophenyl esters or by using either TBTU or di-isopropyl carbodi-imide activation prior to coupling. 20% piperidine in DMF is used for selective removal of Fmoc after each coupling. Cleavage from the resin and final removal of side chain protection is performed by 95% TFA containing appropriate scavengers. The peptides are purified and analysed by reversed phase (C18) HPLC. The identity of the peptides is confirmed by using electro-spray mass spectroscopy (Finnigan mat SSQ710).

Several other well known methods can be applied by a person skilled in the art to synthesise the peptides.

The peptides of the invention may be used in a method for the treatment of Alzheimer's disease and Down syndrome patients with cells producing frameshift mutant βAPP and Ubi-B proteins, which treatment comprises administering at least one peptide of the present invention in vivo or ex vivo to a patient in need of such treatment.

In another embodiment the peptides of the invention may be used to vaccinate a human being disposed for Alzheimer's disease, by administering at least one peptide of the present invention to said human being.

It is further considered to be an advantage to administer to a human a mixture of the peptides of this invention, whereby each of the peptides of the invention can bind to different types of HLA class I and/or class II molecules of the individual.

It is considered that the peptides may be administered together, either simultaneously or separately, with compounds such as cytokines and/or growth factors, i.e. interleukin-2 (IL-2), interleukin-12 (IL-12), granulocyte macrophage colony stimulating factor (GM-CSF), or the like in order to strengthen the immune response as known in the art.

The peptides according to the present invention can be used in a vaccine or a therapeutical composition either alone or in combination with other materials, such as for instance standard adjuvants or in the form of a lipopeptide conjugate which as known in the art can induce high-affinity cytotoxic T lymphocytes, (K. Deres, Nature, Vol.342, (nov.1989)).

The peptides according to the present invention may be useful to include in either a peptide or recombinant fragment based vaccine.

The peptides according to the present invention can be included in pharmaceutical compositions or in vaccines together with usual additives, diluents, stabilisers or the like as known in the art.

According to this invention, a pharmaceutical composition or vaccine may include the peptides alone or in combination with at least one pharmaceutically acceptable carrier or diluent.

Further a vaccine or therapeutical composition can comprise a selection of peptides which are fragments of the mutant βAPP and Ubi-B proteins associated with Alzheimer's disease and Down syndrome.

The vaccine according to this invention may further be administered to the population in general for example as a mixture of peptides giving rise to T cell immunity against cells in which Alzheimer's disease and Down syndrome connected βAPP and Ubi-B frameshift mutations may occur.

The peptides according to this invention may be administered as single peptides or as a mixture of peptides. Alternatively the peptides may be covalently linked with each other to form larger polypeptides or even cyclic polypeptides.

A therapy for Alzheimer's disease and Down syndrome according to the present invention may be administered both in vivo or ex vivo having as the main goal to elicit specific T cell immunity against the mutant βAPP and Ubi-B gene products associated with Alzheimer's disease and Down syndrome.

Further, the frameshift mutant peptides of this invention may be administered to a patient by various routes including but not limited to subcutaneous, intramuscular, intradermal, intraperitoneal, intravenous or the like. In one embodiment the peptides of this invention are administered intradermally. The peptides may be administered at single or multiple injection sites to a patient in a therapeutically or prophylactically effective amount.

The peptides of this invention may be administered only once or alternatively several times, for instance once a week over a period of 1–2 months with a repeated sequence later, all according to the need of the patient being treated.

The peptides of this invention can be administered in an amount in the range of 1 microgram (1 µg) to 1 gram (1 g) to an average human patient or individual to be vaccinated. It is preferred to use a smaller dose in the rage of 1 microgram (1 µg) to 1 milligram (1 mg) for each administration.

The invention further encompasses DNA sequences which encodes a frameshift mutation peptide.

The peptides according to the invention may be administered to an individual in the form of DNA vaccines. The DNA encoding these peptides may be in the form of cloned plasmid DNA or synthetic oligonucleotide. The DNA may be delivered together with cytokines, such as IL-2, and/or other co-stimulatory molecules. The cytokines and/or co-stimulatory molecules may themselves be delivered in the form of plasmid or oligonucleotide DNA. The response to a DNA vaccine has been shown to be increased by the presence of immunostimulatory DNA sequences (ISS). These can take the form of hexameric motifs containing methylated CpG, according to the formula:

5'-purine-purine-CG-pyrimidine-pyrimidine-3'. Our DNA vaccines may therefore incorporate these or other ISS, in the DNA encoding the peptides, in the DNA encoding the cytokine or other co-stimulatory molecules, or in both. A review of the advantages of DNA vaccination is provided by Tighe et al (1998, *Immunology Today*, 19(2), 89–97).

In one embodiment, the DNA sequence encoding the mutant βAPP and mutant Ubi-B peptides comprises:

Normal βAPP gene sequence (exons 9 and 10).
```
                              repeat 1
GAG AGG CTT GAG GCC AAG CAC CGA GAG AGA ATG TCC CAG GTC ATG (SEQ ID NO: 17)

repeat 2
AGA GAA TGG GAA GAG GCA GAA CGT CAA GCA AAG AAC TTG CCT AAA (SEQ ID NO: 18)
```

Mutant βAPP gene sequence, GA deleted from repeat 1.
```
GAG AGG CTT GAG GCC AAG CAC CGA GAG AAT GTC CCA GGT CAT GAG (SEQ ID NO: 19)
AGA ATG GGA AGA GGC AGA ACG TCA AGC AAA GAA CTT GCC TAA
```

Mutant βAPP gene sequence, GA deleted from repeat 2.
```
GAG AGG CTT GAG GCC AAG CAC CGA GAG AGA ATG TCC CAG GTC ATG (SEQ ID NO: 20)
AGA ATG GGA AGA GGC AGA ACG TCA AGC AAA GAA CTT GCC TAA
```

Normal Ubi-B gene (exon) sequence.
```
                              deletion motif
CAC CTG GTC CTG CGT CTG AGA GGT GGT ATG CAG ATC TTC GTG AAG (SEQ ID NO: 21)
ACC CTG ACC GGC AAG ACC ATC ACC CTG GAA GTG GAG CCC AGT GAC
```

Mutant Ubi-B gene sequence, GT deleted from the deletion motif.
```
CAC CTG GTC CTG CGT CTG AGA GGG TAT GCA GAT CTT CGT GAA GAC (SEQ ID NO: 22)
CCT GAC CGG CAA GAC CAT CAC CCT GGA AGT GGA GCC CAG TGA
```

Normal Ubi-B gene (exon 2) sequence.
```
CAC CTG GTC CTG CGT CTG AGA GGT GGT ATG CAG ATC TTC GTG AAG (SEQ ID NO: 23)

CT repeat
ACC CTG ACC GGC AAG ACC ATC ACT CTG GAG GTG GAG CCC AGT GAC (SEQ ID NO: 24)
```

Mutant Ubi-B gene sequence, CT deleted from the CT repeat.
```
CAC CTG GTC CTG CGT CTG AGA GGT GGT ATG CAG ATC TTC GTG AAG (SEQ ID NO: 25)
ACC CTG ACC GGC AAG ACC ATC ACT GGA GGT GGA GCC CAG TGA
```

The invention further encompasses vectors and plasmids comprising a DNA sequence encoding at least one frameshift mutant βAPP and/or Ubi-B peptide. The vectors include, but are not limited to E.Coli plasmid, a Listeria vector and recombinant viral vectors. Recombinant viral vectors include, but are not limited to orthopox virus, canary virus, capripox virus, suipox virus, vaccinia, baculovirus, human adenovirus, SV40, bovine papilloma virus and the like comprising the DNA sequence encoding a mutant βAPP and/or Ubi-B peptide.

It is considered that a treatment for Alzheimer's disease and Down syndrome, or prophylaxis for Alzheimer's disease, may be achieved also through the administration of an effective amount of a recombinant virus vector or plasmid comprising at least one insertion site containing a DNA sequence encoding a frameshift mutant peptide to a patient, whereby the patient's antigen presenting cells are turned into host cells for the vector/plasmid and presentation of HLA/frameshift mutant peptide complex is achieved.

A person skilled in the art will find other possible use combinations with the peptides of this invention, and these are meant to be encompassed by the present claims.

The peptides according to this invention may be produced by conventional processes as known in the art, such as chemical peptide synthesis, recombinant DNA technology or protease cleavage of a protein or peptide encoded by frameshift mutated βAPP gene and Ubi-B gene. One method for chemical synthesis is elucidated in the description below.

Through the present invention the following advantages are achieved:

It offers a possibility to treat patients suffering from Alzheimer's disease and Down syndrome connected with frameshift mutant βAPP and Ubi-B gene products, who known at present do not have any good treatment alternatives.

Furthermore it offers a possibility to vaccinate humans prophylaxtically against the onset of Alzheimer's disease.

---

What is claimed is:

1. An isolated peptide consisting of the amino acid sequence of SEQ ID NO.1.

2. A composition comprising the peptide of claim 1 and a carrier.

* * * * *

SEQUENCE LISTING

<160> NUMBER OF SEQ ID NOS: 25

<210> SEQ ID NO 1
<211> LENGTH: 19
<212> TYPE: PRT
<213> ORGANISM: homo sapiens

<400> SEQUENCE: 1

Asn Val Pro Gly His Glu Arg Met Gly Arg Gly Arg Thr Ser Ser Lys
1               5                   10                  15

Glu Leu Ala

<210> SEQ ID NO 2
<211> LENGTH: 27
<212> TYPE: PRT
<213> ORGANISM: Homo sapiens

<400> SEQUENCE: 2

Arg Leu Glu Ala Lys His Arg Glu Asn Val Pro Gly His Glu Arg Met
1               5                   10                  15

Gly Arg Gly Arg Thr Ser Ser Lys Glu Leu Ala
            20                  25

<210> SEQ ID NO 3
<211> LENGTH: 17
<212> TYPE: PRT
<213> ORGANISM: Homo sapiens

<400> SEQUENCE: 3

Arg Leu Glu Ala Lys His Arg Glu Asn Val Pro Gly His Glu Arg Met
1               5                   10                  15

Gly

<210> SEQ ID NO 4
<211> LENGTH: 12
<212> TYPE: PRT
<213> ORGANISM: Homo sapiens

<400> SEQUENCE: 4

Met Gly Arg Gly Arg Thr Ser Ser Lys Glu Leu Ala
1               5                   10

<210> SEQ ID NO 5
<211> LENGTH: 15
<212> TYPE: PRT
<213> ORGANISM: Homo sapiens

<400> SEQUENCE: 5

Glu Arg Met Ser Gln Val Met Arg Met Gly Arg Gly Arg Thr Ser
1               5                   10                  15

<210> SEQ ID NO 6
<211> LENGTH: 20
<212> TYPE: PRT
<213> ORGANISM: Homo sapiens

<400> SEQUENCE: 6

Tyr Ala Asp Leu Arg Glu Asp Pro Asp Arg Gln Asp His His Pro Gly
1               5                   10                  15

Ser Gly Ala Gln
            20

<210> SEQ ID NO 7
<211> LENGTH: 28
<212> TYPE: PRT
<213> ORGANISM: Homo sapiens

<400> SEQUENCE: 7

His Leu Val Leu Arg Leu Arg Gly Tyr Ala Asp Leu Arg Glu Asp Pro
1               5                   10                  15

Asp Arg Gln Asp His His Pro Gly Ser Gly Ala Gln
            20                  25

<210> SEQ ID NO 8

-continued

```
<211> LENGTH: 17
<212> TYPE: PRT
<213> ORGANISM: Homo sapiens

<400> SEQUENCE: 8

His Leu Val Leu Arg Leu Arg Gly Tyr Ala Asp Leu Arg Glu Asp Pro
1               5                   10                  15

Asp

<210> SEQ ID NO 9
<211> LENGTH: 5
<212> TYPE: PRT
<213> ORGANISM: Homo sapiens

<400> SEQUENCE: 9

Gly Gly Gly Ala Gln
1               5

<210> SEQ ID NO 10
<211> LENGTH: 13
<212> TYPE: PRT
<213> ORGANISM: Homo sapiens

<400> SEQUENCE: 10

Thr Leu Thr Gly Lys Thr Ile Thr Gly Gly Gly Ala Gln
1               5                   10

<210> SEQ ID NO 11
<211> LENGTH: 14
<212> TYPE: DNA
<213> ORGANISM: Homo sapiens

<400> SEQUENCE: 11
accgagagag aatg                                                           14

<210> SEQ ID NO 12
<211> LENGTH: 12
<212> TYPE: DNA
<213> ORGANISM: Homo sapiens

<400> SEQUENCE: 12
catgagagaa tg                                                             12

<210> SEQ ID NO 13
<211> LENGTH: 29
<212> TYPE: PRT
<213> ORGANISM: Homo sapiens

<400> SEQUENCE: 13

Arg Leu Glu Ala Lys His Arg Glu Arg Met Ser Gln Val Met Arg Glu
1               5                   10                  15

Trp Glu Glu Ala Glu Arg Gln Ala Lys Asn Leu Pro Lys
            20                  25

<210> SEQ ID NO 14
<211> LENGTH: 13
<212> TYPE: DNA
<213> ORGANISM: Homo sapiens

<400> SEQUENCE: 14
tctgagaggt ggt                                                            13

<210> SEQ ID NO 15
```

```
<211> LENGTH: 10
<212> TYPE: DNA
<213> ORGANISM: Homo sapiens

<400> SEQUENCE: 15
tcactctgga                                                              10

<210> SEQ ID NO 16
<211> LENGTH: 30
<212> TYPE: PRT
<213> ORGANISM: Homo sapiens

<400> SEQUENCE: 16

His Leu Val Leu Arg Leu Arg Gly Gly Met Gln Ile Phe Val Lys Thr
1               5                   10                  15

Leu Thr Gly Lys Thr Ile Thr Leu Glu Val Glu Pro Ser Asp
            20                  25                  30

<210> SEQ ID NO 17
<211> LENGTH: 45
<212> TYPE: DNA
<213> ORGANISM: Homo sapiens

<400> SEQUENCE: 17
gagaggcttg aggccaagca ccgagagaga atgtcccagg tcatg                       45

<210> SEQ ID NO 18
<211> LENGTH: 45
<212> TYPE: DNA
<213> ORGANISM: Homo sapiens

<400> SEQUENCE: 18
agagaatccg aagaggcaga acgtcaagca aagaacttgc ctaaa                       45

<210> SEQ ID NO 19
<211> LENGTH: 87
<212> TYPE: DNA
<213> ORGANISM: Homo sapiens

<400> SEQUENCE: 19
gagaggcttg aggccaagca ccgagagaat gtcccaggtc atgagagaat gggaagaggc       60
agaacgtcaa gcaaagaact tgcctaa                                           87

<210> SEQ ID NO 20
<211> LENGTH: 87
<212> TYPE: DNA
<213> ORGANISM: Homo sapiens

<400> SEQUENCE: 20
gagaggcttg aggccaagca ccgagagaga atgtcccagg tcatgagaat gggaagaggc       60
agaacgtcaa gcaaagaact tgcctaa                                           87

<210> SEQ ID NO 21
<211> LENGTH: 90
<212> TYPE: DNA
<213> ORGANISM: Homo sapiens

<400> SEQUENCE: 21
cacctggtcc tgcgtctgag aggtggtatg cagatcttcg tgaagaccct gaccggcaag       60
accatcaccc tggaagtgga gcccagtgac                                        90
```

-continued

```
<210> SEQ ID NO 22
<211> LENGTH: 87
<212> TYPE: DNA
<213> ORGANISM: Homo sapiens

<400> SEQUENCE: 22
cacctggtcc tgcgtctgag agggtatgca gatcttcgtg aagaccctga ccggcaagac      60
catcaccctg gaagtggagc ccagtga                                          87

<210> SEQ ID NO 23
<211> LENGTH: 45
<212> TYPE: DNA
<213> ORGANISM: Homo sapiens

<400> SEQUENCE: 23
cacctggtcc tgcgtctgag aggtggtatg cagatcttcg tgaag                      45

<210> SEQ ID NO 24
<211> LENGTH: 45
<212> TYPE: DNA
<213> ORGANISM: Homo sapiens

<400> SEQUENCE: 24
accctgaccg gcaagaccat cactctggag gtggagccca gtgac                      45

<210> SEQ ID NO 25
<211> LENGTH: 87
<212> TYPE: DNA
<213> ORGANISM: Homo sapiens

<400> SEQUENCE: 25
cacctggtcc tgcgtctgag aggtggtatg cagatcttcg tgaagaccct gaccggcaag      60
accatcactg gaggtggagc ccagtga                                          87
```